United States Patent [19]
Rosen

[11] 3,973,029
[45] * Aug. 3, 1976

[54] HYPERGLYCEMIA THERAPY II

[75] Inventor: Harry Rosen, Drexel Hill, Pa.

[73] Assignee: American Home Products Corporation, New York, N.Y.

[ * ] Notice: The portion of the term of this patent subsequent to Dec. 23, 1992, has been disclaimed.

[22] Filed: May 19, 1975

[21] Appl. No.: 578,794

Related U.S. Application Data

[63] Continuation of Ser. No. 497,805, Aug. 15, 1974, abandoned.

[52] U.S. Cl. .................................................. 424/273
[51] Int. Cl.² ...................................... A61K 31/415

[58] Field of Search ...................................... 424/273

[56] References Cited
UNITED STATES PATENTS
3,803,155   4/1974   Sulkowski et al. .................. 424/273

*Primary Examiner*—Jerome D. Goldberg
*Attorney, Agent, or Firm*—Stephen Venetianer

[57] ABSTRACT

The invention relates to a method of treating hyperglycemia in warm-blooded animals which utilizes administration to warm-blooded animals of a compound selected from the group of compounds defined below.

1 Claim, No Drawings

HYPERGLYCEMIA THERAPY II

This is a continuation of application Ser. No. 497,805, filed Aug. 15, 1974 and now abandoned.

DESCRIPTION OF THE INVENTION

It has been discovered that a particular group of compounds previously known to be useful primarily as anti-depressants, suprisingly are highly effective in relieving hyperglycemia in warm-blooded animals. The invention resides in the method of treating hyperglycemia in a warm-blooded animal by administering to the animal a therapeutically active amount of a compound selected from the group consisting of those having the following general formulae:

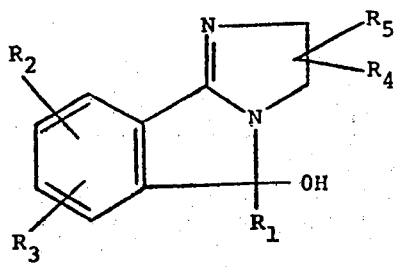
(I)

and

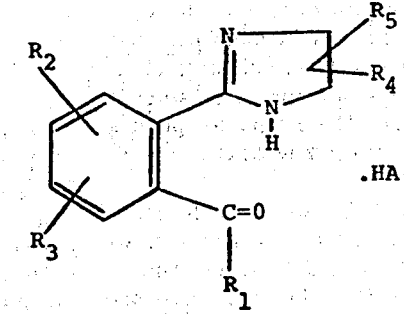
(II)

wherein $R_4$ and $R_5$ are each lower alkyl and attached to the same carbon atom; $R_2$ is selected from the group consisting of hydrogen, halogen, amino, lower alkylamino, lower alkyl, and lower alkoxy; $R_3$ is hydrogen when $R_2$ and $R_3$ are dissimilar and when $R_2$ and $R_3$ are the same they are both selected from the group consisting of hydrogen, halogen, lower alkyl, and lower alkoxy; $R_1$ is selected from the group consisting of phenyl, monohalophenyl, dihalophenyl, trifluoro-methylphenyl, mono(lower)alkoxyphenyl, and di(lower)alkoxyphenyl; and HA is a pharmaceutically acceptable acid. Such compounds are disclosed in U.S. Pat. No. 3,803,155, granted Apr. 9, 1974, and incorporated herein by reference.

The compounds of formulae (I) and (II) are prepared by reacting a substituted phthalimidine according to the folowing procedure:

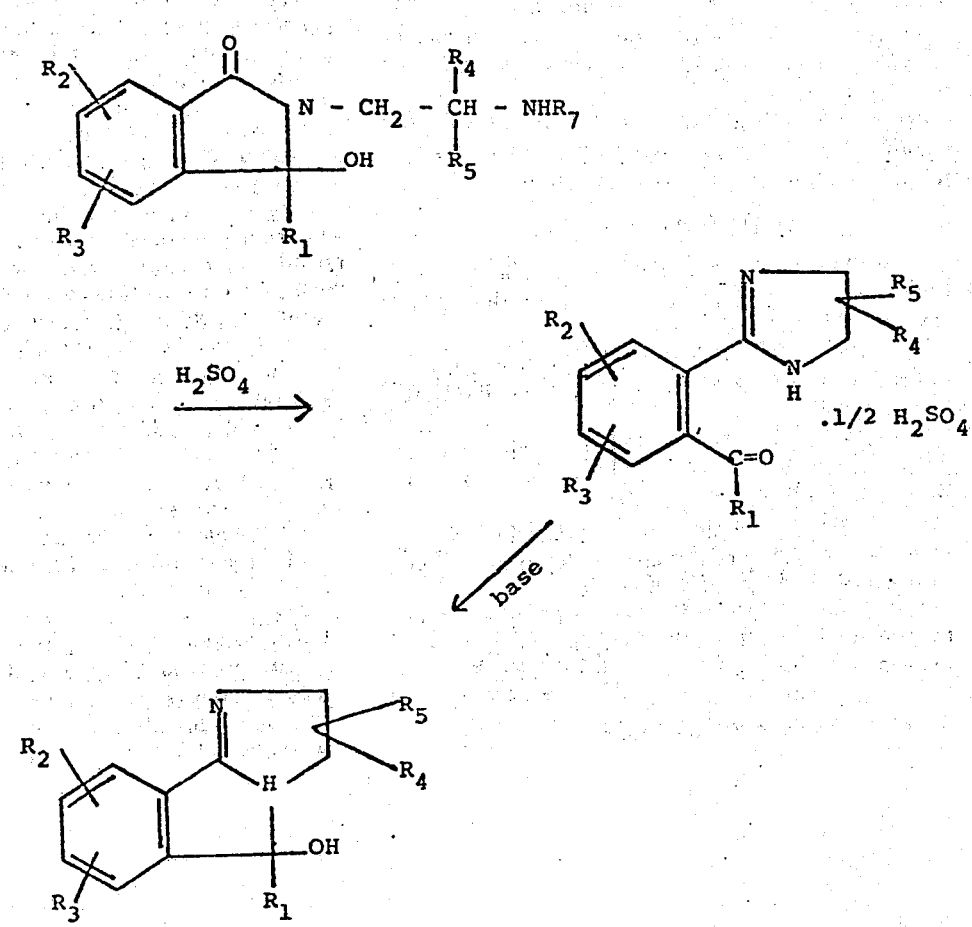

In the above reaction sequence, $R_1$, $R_2$, $R_3$, $R_4$ and $R_5$ are defined as above and $R_7$ is lower alkylsulfonyl, phenylsulfonyl, monohalophenylsulfonyl, dihalophenylsulfonyl, mono(lower)alkylphenylsulfonyl, di(lower)alkoxyphenylsulfonyl.

As employed herein the term (lower)alkyl includes straight and branched chain hydrocarbon moieties of from 1 to about 4 carbon atoms such as methyl, ethyl, propyl, i-propyl and butyl. The term (lower)alkoxy includes hydrocarbonoxy groups which contain from 1 to about 6 carbon atoms such as methoxy, ethoxy, propoxy, butoxy and hexoxy. The term "halogen" and "halo" as used herein include bromine, fluorine, chlorine and iodine.

The substituted phthalimidines can be prepared by the sulfonylation of the intermediate phthalimidine compound. The intermediate phthalimidines are readily prepared by reacting a Ψ acid chloride of an o-aroyl benzoic acid with the appropriate substituted ethylene diamine compound. These type compounds are described in the literature (Sulkowski et al J. Org. Chem. 32, 2180).

They are cyclized to a 2-(2-imidazoline-2-yl)benzophenone by treatment with sulfuric acid according to the procedure outlined above and treatment with a base affords the corresponding dihydroimidazoisoindolols.

TEST METHOD

Male rats weighing 170–200 grams are fasted overnight, a control blood sample is taken from the tail and a test dose of 60 mg/kg is administered by stomach tube. Subsequent blood samples are taken at hourly intervals for five hours. Four rats were used in each of the following tests except the first wherein eight rats were used.

In general, a compound is considered active if a depression in blood sugar approximating 20% is observed for at least 3 of the 5 hour test period.

COMPOUNDS TESTED 1. 4-chloro-2'-(5,5-dimethyl-2-imidazolin-2-yl)benzophenone hydrochloride; $R_1$=parachlorophenyl; $R_2$ and $R_3$=H; $R_4$ and $R_5$=methyl 2. 2-[4,4(or 5,5)-dimethyl-2-imidazolin-2-yl]benzophenone hydrochloride; $R_1$=phenyl; $R_2$ and $R_3$=H; $R_4$ and $R_5$=methyl 3. 4-bromo-2'-[4,4 (or 5,5)-dimethyl-2-imidazolin-2-yl]benzophenone hydrochloride; $R_1$=p-bromophenyl; $R_2$ and $R_3$=H; $R_4$ and $R_5$=methyl 4. 2-[4,4(or 5,5)-dimethyl-2-imidazolin-2-yl]-4'-fluorobenzophenone hydrochloride; $R_1$=p-fluorophenyl; $R_2$ and $R_3$=H; $R_4$ and $R_5$=methyl 5. 2-[4,4(or 5,5)-dimethyl-2-imidazolin-2-yl]-4'-trifluoromethyl benzophenone hydrochloride; R= p-trifluoromethyl; $R_2$ and $R_3$=H; $R_4$ and $R_5$=methyl 6. 2,5-dihydro-2,2(or 3,3)-dimethyl-5-(m-trifluoromethylphenyl)-3H-imidazo[2,1-a,]isoindol; $R_1$=m-trifluoromethylphenyl; $R_2$ and $R_3$=H; $R_4$ and $R_5$=methyl

TEST RESULTS

| Compound | Dose mg/kg | Per Cent Change in Blood Sugar, hours | | | | |
|---|---|---|---|---|---|---|
| | | 1 | 2 | 3 | 4 | 5 |
| 1 | 60 | −19 | −22 | −23 | −19 | −12 |
| | 30 | −21 | −27 | −30 | −30 | −36 |
| | 15 | −31 | −43 | −35 | −36 | −32 |
| | 7.5 | −18 | −22 | −23 | −20 | −15 |
| | 3.75 | +7 | −9 | −19 | −18 | −16 |
| | 1.9 | +9 | 0 | +2 | +3 | 0 |
| 2 | 15 | −35 | −55 | −45 | −35 | −30 |
| | 7.5 | 0 | −31 | −18 | −9 | −7 |
| | 3.75 | −9 | −6 | −4 | +3 | +4 |
| 3 | 15 | −25 | −46 | −34 | −32 | −29 |
| 4 | 15 | −46 | −55 | −56 | −52 | −39 |
| 5 | 60 | +13 | +8 | −2 | −14 | −12 |
| 6 | 60 | −19 | −43 | −47 | −46 | −46 |
| | 30 | −8 | −37 | −43 | −47 | −42 |
| | 1.5 | −4 | −21 | −31 | −33 | −32 |
| | 7.5 | +20 | 0 | −6 | −11 | −12 |

The surprising efficacy of the compounds of formulae I and II above in the test described hereinbefore has clearly indicated that they are active anti-hyperglycemic agents.

In the exercising of the method of the invention, the compounds of formulae I and II used therein may be administered alone or in combination with pharmaceutically acceptable carriers, the proportion of which is determined by the solubility and chemical nature of the compound selected, the chosen route of administration and standard pharmaceutical practice. For example, they may be administered orally in the form of tablets or capsules, which may contain conventional excipients, or in the form of solutions; or they may be injected parenterally, that is intramuscularly, intravenously or subcutaneously. For parenteral administration, they may be used in the form of sterile solutions, containing other solutes, for example, enough saline or glucose to make the solutions isotonic.

The dosage of the present therapeutic agent will vary with the form of administration and the particular compound chosen. It will generally be found that when the composition is administered orally, larger quantities of the active agent will be required to produce the same effect as a smaller quantity given parenterally. In general, the compounds of this invention are most desirably administered at a concentration level that will generally afford effective results without causing any harmful or deleterious side effects.

The compounds of the present invention, when tested in accordance with the test procedure given in detail hereinbefore, are effective to relieve hyperglycemia at dosages in the range of about 10 to about 70 mg/kg. of body weight of the animals tested.

I claim:

1. The method of treating hyperglycemia in a warm-blooded animal suffering from hyperglycemia which comprises orally or parenterally administering to said animal an effective amount for treating hyperglycemia of a compound of the following formulae

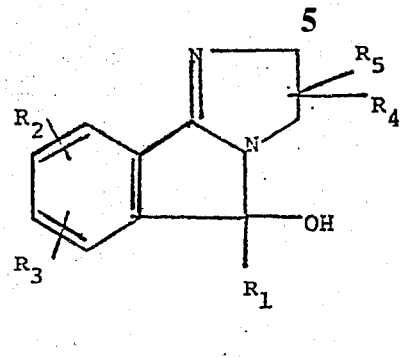 and 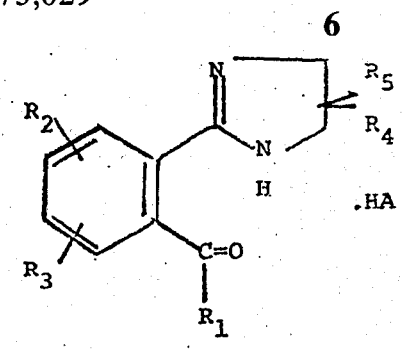

wherein $R_4$ and $R_5$ are each lower alkyl and attached to the same carbon atom; $R_2$ is selected from the group consisting of hydrogen, halogen, amino, lower alkylamino, lower alkyl, and lower alkoxy; $R_3$ is hydrogen when $R_2$ and $R_3$ are dissimilar and when $R_2$ and $R_3$ are the same they are both selected from the group consisting of hydrogen, halogen, lower alkyl, and lower alkoxy; $R_1$ is selected from the group consisting of phenyl, monohalophenyl, dihalophenyl, trifluoro-methylphenyl, mono(lower)alkoxyphenyl, and di(lower)alkoxyphenyl; and HA is a pharmaceutically acceptable acid.

* * * * *